United States Patent [19]

Swick et al.

[11] Patent Number: 5,253,538
[45] Date of Patent: Oct. 19, 1993

[54] METHOD AND DEVICE FOR QUANTIFYING PARTICLES ON A SURFACE

[75] Inventors: Robert H. Swick, New Castle, Del.; Gene J. Sullivan, LaFayette, Calif.; Donald G. Lutz, San Ramon; Richard S. Dryden, San Jose, Calif.

[73] Assignee: Dryden Engineering Co., Inc., Santa Clara, Calif.

[21] Appl. No.: 692,157

[22] Filed: Apr. 26, 1991

[51] Int. Cl.$^5$ .................................. G06M 11/00
[52] U.S. Cl. .............................. 73/864.34; 73/104; 73/863.23; 73/864.33; 73/864.73; 377/10; 250/222.2
[58] Field of Search ........... 73/863.21, 863.23, 863.24, 73/863.25, 104, 864.33, 864.34, 864.35, 864.73, 864.74, 865.5; 377/10, 12; 250/574, 222.2

[56] References Cited

U.S. PATENT DOCUMENTS

| | | | |
|---|---|---|---|
| 1,791,760 | 2/1931 | Kline | 15/421 X |
| 1,992,238 | 2/1935 | Rose | 15/157 |
| 2,027,543 | 1/1936 | Lofgren | 15/157 |
| 2,181,487 | 11/1939 | Khuen-Kryk | 15/155 |
| 2,528,278 | 10/1950 | Kendrick | 15/420 |
| 2,864,119 | 12/1958 | Crise | 15/404 |
| 2,885,716 | 5/1959 | Brown, Jr. | 15/417 |
| 2,966,694 | 1/1961 | Brown, Jr. | 15/417 |
| 3,067,619 | 12/1962 | Fielding | 73/864.33 |
| 3,273,187 | 9/1966 | Williams | 15/1.7 |
| 3,362,141 | 1/1968 | Royster, Jr. et al. | 73/864.33 X |
| 3,431,423 | 3/1969 | Keller | 377/10 X |
| 3,662,605 | 5/1972 | Grotyohann | 73/864.33 |
| 3,678,487 | 7/1972 | Ludewig, Jr. et al. | 73/865.5 X |
| 3,748,905 | 7/1973 | Zahlava | 73/864.33 X |
| 3,765,771 | 10/1973 | Shaw | 377/10 |
| 3,805,591 | 4/1974 | Willis et al. | 73/865.5 X |
| 3,868,222 | 2/1975 | Barringer | 23/230 EP |
| 4,184,291 | 1/1980 | Marton | 51/170 R |
| 4,395,676 | 7/1983 | Hollinger et al. | 377/10 X |
| 4,455,881 | 6/1984 | Clark et al. | 73/863.23 X |
| 4,482,864 | 11/1984 | Koenig et al. | 324/226 |
| 4,502,951 | 3/1985 | Koenig et al. | 209/21 |
| 4,616,513 | 10/1986 | Gibson et al. | 73/863.23 |
| 4,631,483 | 12/1986 | Proni et al. | 73/864.11 X |
| 4,893,320 | 1/1990 | Yanagi et al. | 377/11 |
| 4,928,537 | 5/1990 | Liu et al. | 377/10 X |
| 4,967,608 | 11/1990 | Yost | 73/865.5 X |

FOREIGN PATENT DOCUMENTS

| | | | |
|---|---|---|---|
| 157684 | 8/1985 | Japan | 377/10 |
| 110280 | 5/1986 | Japan | 377/10 |
| 265137 | 10/1989 | Japan | 73/864.34 |

Primary Examiner—Tom Noland
Attorney, Agent, or Firm—Limbach & Limbach

[57] ABSTRACT

A device and method for counting particles on a sample surface. The device includes a scanner having a surface for interfacing with the sample surface. The scanner is connected to one end of a tube which has two canals. The other end of the tube is connected to the particle counter. One of the tube canals supplies air from the particle counter through holes in the scanner surface for dislodging and fluidizing particles on the sample surface. The other tube canal returns air with the sample surface particles to the particle counter. After the particles are counted they are removed from the air stream by a filter. The air is then recycled back through the supply canal of the tube to facilitate additional particle counting. The method for using the device involves passing the scanner over the sample surface for predetermined periods, and collecting, counting and computing the average relative number of particles per unit area.

27 Claims, 3 Drawing Sheets

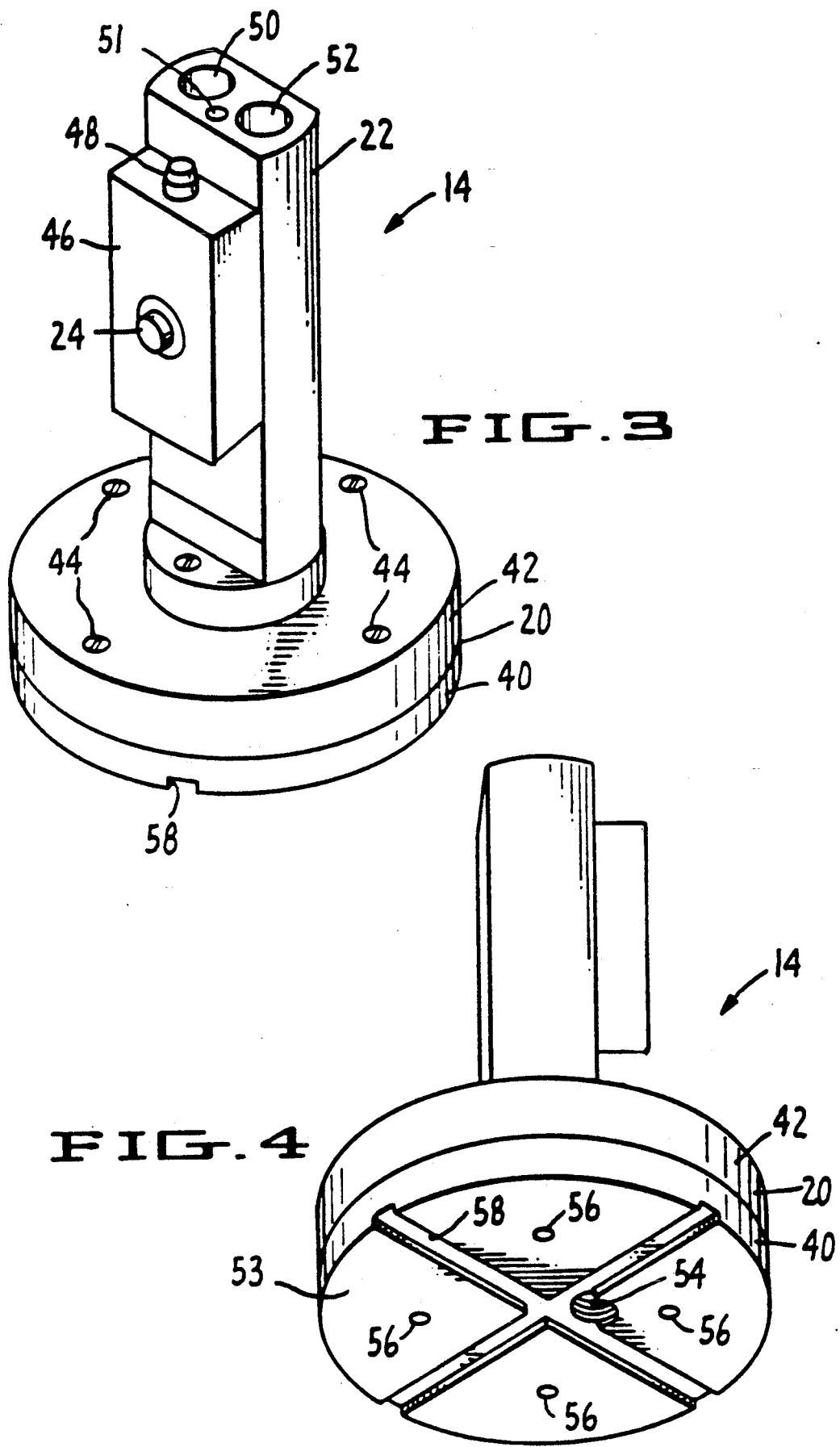

METHOD AND DEVICE FOR QUANTIFYING PARTICLES ON A SURFACE

FIELD OF THE INVENTION

The invention relates to particle counting. In particular, the invention involves a method and device for moving particles off of a surface and into a particle counter for the purpose of ascertaining contamination levels.

BACKGROUND OF THE INVENTION

Contamination detection and quantitation requirements have become increasingly important, particularly with the rapid evolution of the highly technical industries. For example, the semiconductor industry has developed technology for precisely producing microelectronic devices. In order to reliably produce such products, highly stringent contamination standards must be maintained in the production facilities.

In an effort to control and minimize contamination in crucial stages of a production process, "cleanrooms" are frequently used. A cleanroom is a room in which the air filtration, air distribution, utilities, materials of construction, equipment, and operating procedures are specified and regulated to control airborne particle concentrations to meet appropriate airborne particulate cleanliness classifications. Existing inspection and sampling techniques are inadequate for quickly verifying cleanliness. IES-RP-CC-018-89-T, Sec. 6, p. 7.

Currently there are two primary types of test procedures which are recommended for detecting particles on a cleanroom surface. First, there are visual inspection techniques using ultraviolet or oblique white light. Ultraviolet light is employed to take advantage of the fact that certain organic particles fluoresce. Alternatively, white light is shined towards the test surface at an angle so as to produce reflections which can be visualized. While the white light technique is slightly more sensitive than the ultraviolet technique, they both suffer from the same limitations. These visual inspection techniques only allow a cursory inspection of the surface conditions. They do not provide quantitative data. Also, the visual inspection techniques, at best, only detect particles which are larger than twenty microns. It is often desirable to detect particles which are less than one micron.

The second type of recommended testing procedure involves removing particles from a test surface, by for example, applying a piece of adhesive tape to the test surface. The particles on the tape are then manually quantitated by putting the tape under a microscope and visually counting the particles. This technique allows the detection of particles of approximately five microns or larger. The primary disadvantage of this technique is that it is very time consuming, and that it is highly sensitive to variability between operators. Given the advanced state of technology today, it is surprising that no more advanced techniques for detecting and quantitating contamination on processing surfaces, have been developed to address these fundamental objectives.

SUMMARY OF THE INVENTION

The present invention provides a device and method for quantitating particles on a sample surface. The device of the present invention includes a scanner having at least one opening for receiving particles from the sample surface. The scanner is connected to a tube having first and second ends. The first end of the tube is connected to the scanner and the second end of the tube is connected to a particle counter which employs optical laser technology. The particle counter includes a vacuum generator which causes air to flow from the sample surface through the scanner, through the tube and into the particle counter, where particles contained in the air stream are counted.

The method of the present invention involves the use of the above mentioned particle counting device. A background particle level of zero is first established by holding the scanner near the cleanroom supply air and taking repeated readings, or by installing an optional zero count filter in the particle counter. Next, the hand-held scanner is passed over the sample surface at a constant rate for a predetermined test period. The test cycle is started by pushing the run switch which is located on the scanner. The particle counter counts and reads out a number corresponding to the average number of particles per unit area. The process is usually repeated several times along adjacent surface areas, each time yielding a "test reading".

BRIEF DESCRIPTION OF THE DRAWINGS

FIG. 3 is a perspective view of the scanner portion of an embodiment of the present invention.

FIG. 4 is a perspective view of the scanner portion of an embodiment of the present invention.

DETAILED DESCRIPTION OF THE PREFERRED EMBODIMENTS

The present invention advantageously employs in operable combination three primary elements to provide the flexibility of sampling particles on a wide variety of surfaces, while also providing relative quantitative data with a high degree of precision and repeatability. In broad terms, the invention involves the combination of a state-of-the-art particle counter connected to a specially designed sampling scanner via a flexible tube. In a preferred embodiment the tube has two canals, one for supplying air to the sample surface, the other for returning the air to the particle counter with particles from the sample surface for quantitation. The light weight moveable scanner and flexible tube design allow particle sampling on many different types of accessible surfaces.

Figure 1:
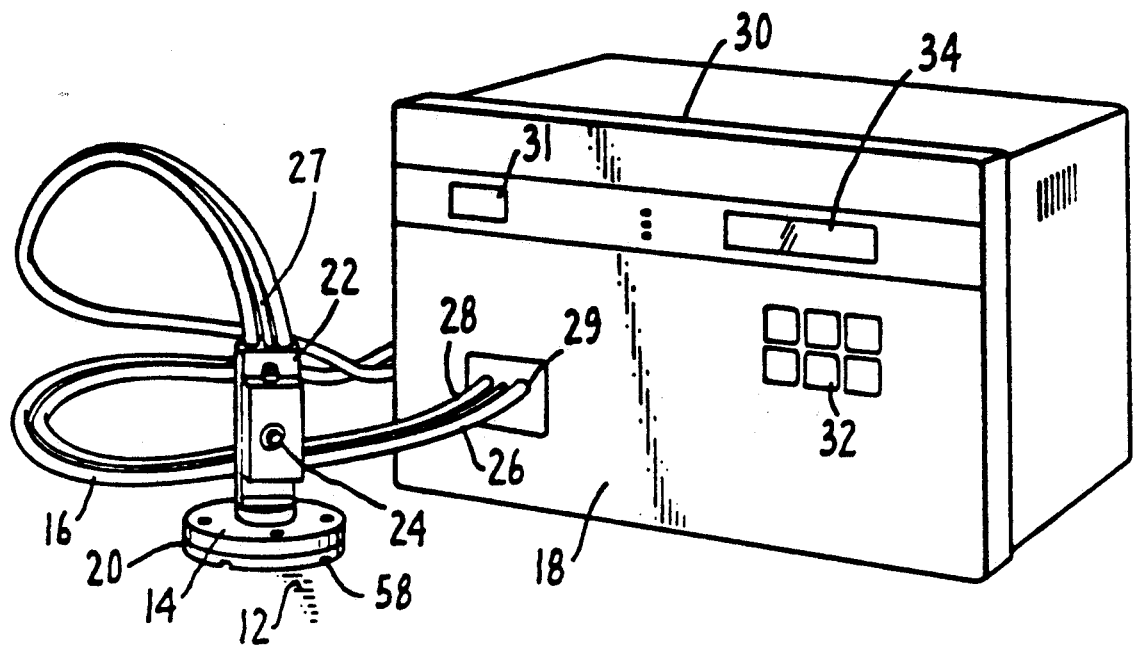
FIG. 1 is a perspective view of an embodiment of the particle counting device of the present invention.

FIG. 1 shows the primary components of one embodiment of the present invention. As shown, the particle counting device 10 is designed to quantitate particles on a sample surface 12. The sample surface 12, as shown, is substantially flat. However, the sample surface may also be curved or angular. Similarly, as shown in FIG. 1, the sample surface 12 is smooth. However, the claimed invention is applicable to other sample surfaces having irregular or textured surfaces. The device includes a scanner 14 connected to a plurality of tubes 16. The two tubes are connected to a particle counter 18.

Figure 2:
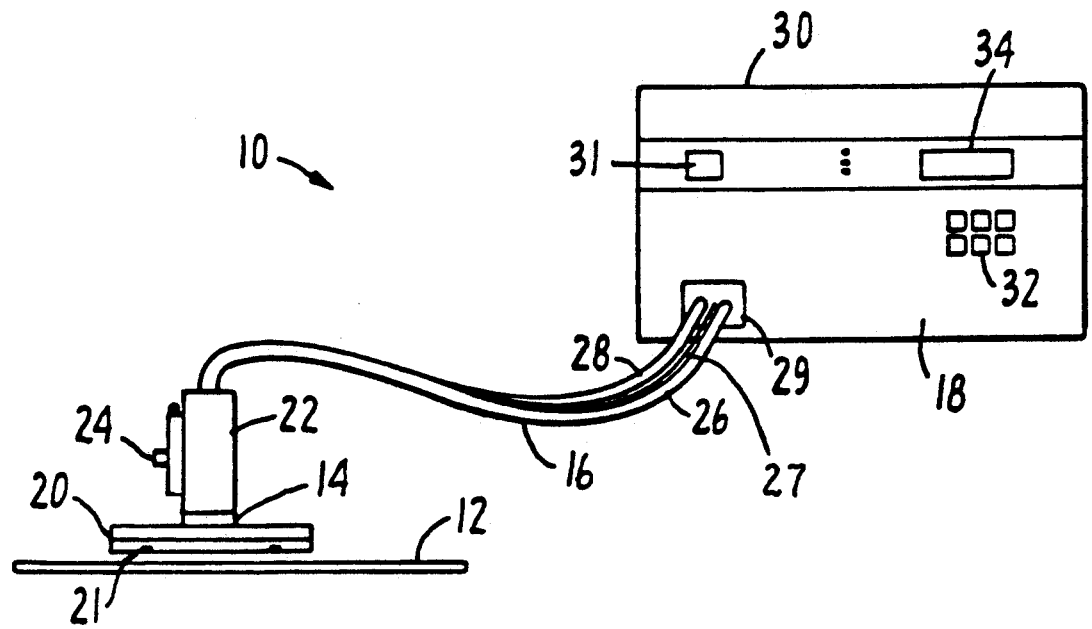
FIG. 2 is a schematic diagram of an embodiment of the particle counting device of the present invention.

The same device embodiment is also illustrated in FIG. 2. The scanner 14 has a substantially planar base 20. The scanner base 20 has a bottom side 21 for interfacing with the sample surface 12. The scanner base 20 is perpendicularly connected to a scanner handle 22 which has a run switch 24 for turning the particle counting device on and off. The tube portion 16 of the device has two canals 26 and 28. Each tube canal 26 and 28 has a first and a second end. The first ends of the tube canals are connected to the scanner handle 22. The second ends of the tube canals 26 and 28 are connected to a port 29 in the particle counter 18. A third conduit 27 contains wires which electrically connect the scanner to the particle counter. The particle counter 18 includes a housing 30, a power switch 31, a control panel 32, and a numerical display 34 for reporting the particle count data. In a preferred embodiment the particle counter also includes software for converting numbers of particles per unit air volume to numbers of particles per unit area relative to the sample surface.

FIG. 3 shows a more detailed view of the scanner portion of the device in a preferred embodiment of the present invention. The base portion 20 of the scanner 14 has two coin-shaped portions 40 and 42 which are fastened together by screws 44. The scanner embodiment shown in FIG. 3 is designed primarily for picking up particles off of a substantially flat surface. However, the claimed invention is not limited to scanners having a substantially flat base. The claimed invention is intended to include scanners of other shapes, which are specifically designed to conform to non-flat sample surfaces. Coin-shaped portion 40 of the scanner base 20 is also referred to as a face plate, and is preferably made of a material which is impregnated with a friction limiting non-particulating substance, for example, hard black anodized aluminum with Teflon impregnation, type 3, class 2, mil spec A8625D. The scanner base 20 is perpendicularly connected to the scanner handle 22 which includes a control section 46 having a run switch 24 and an LED light 48 for indicating whether the device is turned on or off. In a preferred embodiment of the invention, audible signals are also produced to indicate when the instrument is switching between its "counting" and its "standby" modes. The control section 46 is mounted on the side of the scanner handle 22 which also has two bores 50 and 52 for receiving the supply and return canals of the tube 16. Another hole 51 is provided in the handle 22 for receiving the electrical wiring from the particle counter.

FIG. 4 is a perspective view of the bottom side 53 of the face plate portion 40 of the scanner base 20. The scanner base face plate bottom side 53 is designed to interface with the sample surface 12. In this embodiment, the bottom side 53 has a hole 54 which is located approximately in the center of the face plate bottom side. The hole 54 is connected to the bore 50 in the scanner handle 22 which is connected to the return canal of the tube 16. Particles from the sample surface 12 are sucked through the face plate hole 54 for the purpose of counting the particles in the particle counter 18. The face plate bottom side 53 also has a plurality of smaller holes 56 which converge into the scanner handle bore 52 which is connected to the air supply canal of the tube 16. Air is supplied from the particle counter and delivered through the face plate holes 56 onto the sample surface 12 for dislodging and fluidizing particles so that they may be sucked through face plate hole 54 for counting. Face plate bottom side 53 also has intersecting grooves 58 for channeling dislodged particles into face plate hole 54.

Figure 5:
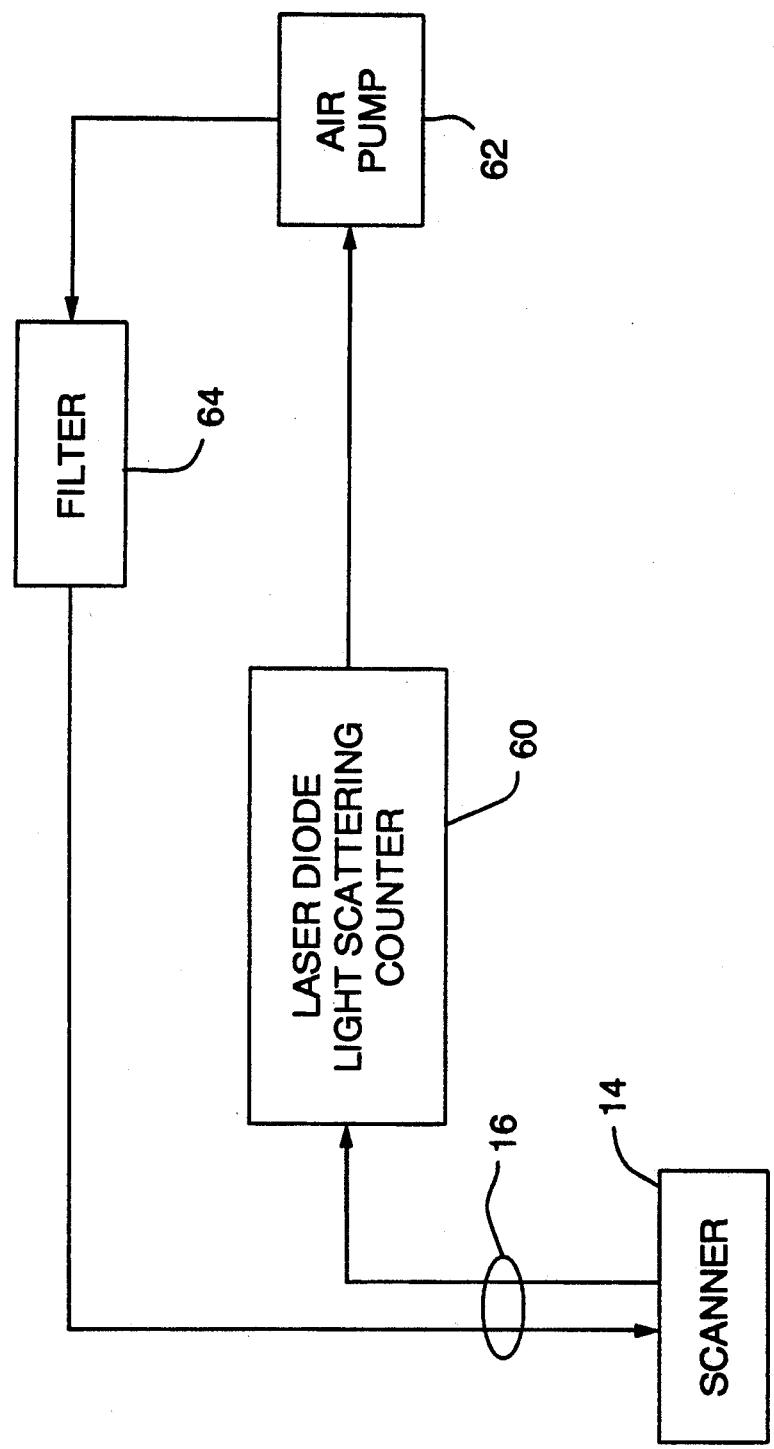
FIG. 5 is a schematic diagram of the particle counting device of the present invention.

FIG. 5 illustrates the air flow path of the particle counting device 10. Air is supplied to and taken in from the scanner 14 through tubes 16. The intake air from the scanner is supplied to a particle counter 60, for example, a laser diode light scattering counter. The intake air with particles from the sample surface is drawn through the particle counter 60 by an air pump 62. An intake of the air pump 62 is plumbed to the discharge side of the particle counter 60. The air pump 62 creates a partial vacuum through the particle counter 60 and one of the tubes 16 to the scanner opening 54. Air drawn into the scanner opening carries particles to the particle counter for counting. Plumbed to the discharge side of the air pump 62 is a filter 64 that filters out particles from the air. The discharge side of the filter 64 is plumbed to the other one of the tubes 16 to supply filtered air to the exhaust holes 56 of the scanner.

The device described above is used to obtain a relative cleanliness level by quanitating the released particles from surfaces. Examples of possible test surfaces include tables, shelves, walls, ceilings, benches, product containers or virtually any other kind of surface. Different scanner geometries can be employed for customizing the device to the particular sample surface of interest. The technique can be used to verify cleanliness prior to undertaking some type of clean room procedure. The technique can also be used to evaluate or compare the effectiveness of various cleaning techniques and products.

In a preferred embodiment of the invention filtered air is used to disturb the surface particles and a vacuum system collects the particles which are fluidized by the air. Particle levels are measured and recorded in particles per centimeters squared or particles per inch squared using optical/laser technology. The device of the present invention is capable of detecting particles as small as 0.3 microns.

A surface particle detector is used which consists of a hand-held scanner with remote run switch, tubing, and a laser based counting system. One CFM of air which is filtered to 0.2 microns, is supplied to the scanner head and the same amount is pulled through the scanner head to the sensing system for counting and sizing.

Prior to counting particles, the system should first be checked for zero counting by holding the scanner head towards the clean room supply air and taking repeated counts until the levels are below 5 particles per inch squared, or by installing the optional zero count filter.

The scanner head is then passed over the sample surface at a rate of 10 LFPM (3 LMPM) for a period of one, three or six seconds. The test cycle is started from the run switch located in the scanner head. The head is moved lightly across the surface assisted by the fluidizing air.

As this method gives relative cleanliness levels immediately, it is recommended that routine monitoring be performed with historical data being logged for various surfaces and locations in the clean room. It is also recommended that a minimum of six readings be taken for any given area with average levels and maximum allowable single reading levels being established for the various surfaces and areas.

While the preferred embodiments have been described in detail above, as shown in the following claims, the claimed invention is intended to include variations of the above described invention which would be obvious to a person having ordinary skill in the art.

We claim:

1. A device for counting particles on a sample surface, comprising:
   a scanner having at least one opening for receiving particles from the sample surface;
   a tube having first and second ends, the first end of the tube being connected to the scanner;
   a particle counter connected to the second end of the tube; and
   means for producing a first fluid stream flowing through the scanner opening and the tube in a direction from the sample surface to the particle counter, for carrying the particles to the counter for quantitation.

2. The device of claim 1, wherein the tube is flexible.

3. The device of claim 1, wherein the tube has two separate canals, one canal being for supplying air to the scanner, the other canal being for returning air from the scanner to the particle counter.

4. The device of claim 1, further comprising:
   means for dislodging and fluidizing particles from the sample surface.

5. The device of claim 4, wherein the tube has two canals and the scanner has a second opening, the dislodging and fluidizing means including a means for producing a second fluid stream flowing through one of the tube canals in a direction from the particle counter to the sample surface.

6. The device of claim 1, wherein the scanner has a substantially flat face for interfacing with the sample surface when the device is in operation.

7. The device of claim 6 wherein the scanner face has a plurality of exhaust air holes for supplying air to the sample surface.

8. The device of claim 7 wherein the scanner face has grooves disposed therein to channel air from the exhaust air holes to the scanner opening.

9. The device of claim 8 wherein the exhaust air holes are arranged substantially circumferentially relative to the scanner opening.

10. The device of claim 1, wherein the scanner includes a substantially planar base having a bottom side and a top side, and a handle appended to the top side of the base.

11. The device of claim 10, wherein the device has a counting mode and a standby mode, and the scanner handle has a run switch for controlling the fluid flow through the counting and standby modes.

12. The device of claim 10, wherein the bottom side of the scanner base is impregnated with a friction limiting non-particulating substance.

13. The device of claim 1, wherein the tube has an air supply canal for delivering air from the particle counter to the sample surface, and an air return canal for returning air from the sample surface to the particle counter, the particle counter including a filter for removing particles from the return canal air before recycling the air back through the supply canal.

14. The device of claim 1 wherein the particle counter is a laser diode light scattering counter.

15. The device of claim 1, further comprising a means for cycling air in a loop between the particle counter and the scanner.

16. A device for counting particles on a sample surface, comprising:
   a substantially flat scanner face having a first opening for receiving air and a second opening for delivering air to the sample surface;
   a particle counter connected to the scanner face, the particle counter having a pump for sucking air through the first scanner face opening, and a filter for removing particles from air before it is delivered to the sample surface through the second scanner face opening.

17. The device of claim 16 wherein the air circulation system is closed so that the same air which is sucked in through the first scanner opening is recycled through the second scanner opening after particle counting and filtration.

18. A method of quantitating particles on a sample surface comprising the steps of:
   providing a particle counting device including a particle counter connected to a flexible tube which is connected to a scanner having a substantially planar surface for interfacing with the sample surface;
   passing air from the sample surface through the scanner and tube into the particle counter for carrying particles to the counter.

19. The method of claim 18 further comprising the step of recycling the air which carries the particles from the sample surface, by filtering out the particles and returning the air to the sample surface.

20. The method of claim 19 further comprising the step of dislodging and fluidizing particles from the sample surface, by directing the returning air through a plurality of holes in the scanner surface so as to dislodge and fluidize the particles into the air which flows into the particle counter.

21. A device for counting particles on a sample surface, comprising:
   a particle-gathering scanner having intake and exhaust holes therein;
   means for intaking air into the intake hole of the scanner and for supplying the intake air to a particle counter;
   a particle counter for counting particles in the intake air; and
   means for exhausting air out the exhaust hole in the scanner.

22. A device as recited in claim 21 further including means for supplying the intake air after it has passed through the particle counter to the means for exhausting air out the exhaust hole in the scanner.

23. A device as recited in claim 21 wherein the particle counter has an intake and a discharge and wherein the means for intaking and supplying air to the particle counter includes a tube coupled at one end to the intake hole of the scanner and at the other end to the intake of the particle counter and further includes an air pump having an inlet coupled to the discharge of the particle counter.

24. A device as recited in claim 23 wherein the means for exhausting air includes a tube coupled at one end to a discharge of the air pump and at the other end to the exhaust hole of the scanner.

25. A device as recited in claim 24 further comprising a filter disposed between the discharge of the particle counter and the exhaust hole of the scanner.

26. A method of quantitating particles on a sample surface comprising the steps of:
   providing a particle counting device including a particle counter coupled to a particle-collecting scanner;
   positioning the scanner adjacent the sample surface;

exhausting air out an exhaust hole in the scanner to dislodge particles on the sample surface proximate the scanner;

collecting the dislodged particles by intaking air into an intake hole in the scanner; and supplying the intake air and dislodged particles to the particle counter.

27. The method as recited in claim 26 further including the step of recycling the intake air by filtering out the particles and returning the air to the sample surface through the exhaust hole in the scanner.

* * * * *